(12) United States Patent
Tsukashima et al.

(10) Patent No.: US 7,206,624 B2
(45) Date of Patent: Apr. 17, 2007

(54) HYDRATION MONITORING CIRCUITRY FOR PH SENSORS

(75) Inventors: Ross Tsukashima, San Diego, CA (US); Erich H. Wolf, Vista, CA (US); Jeffery D. Schipper, Ramona, CA (US); Charles S. Bankert, Oceanside, CA (US); Leo R. Roucher, Rancho Santa Fe, CA (US); Thomas Germain Wallner, San Marcos, CA (US)

(73) Assignee: Sierra Medical Technology, Inc., Poway, CA (US)

( * ) Notice: Subject to any disclaimer, the term of this patent is extended or adjusted under 35 U.S.C. 154(b) by 5 days.

(21) Appl. No.: 11/137,459

(22) Filed: May 25, 2005

(65) Prior Publication Data

US 2006/0270936 A1 Nov. 30, 2006

(51) Int. Cl.
*A61B 5/05* (2006.01)
*A61B 5/00* (2006.01)
*G01N 27/416* (2006.01)
*G01N 27/26* (2006.01)
*G01N 33/50* (2006.01)

(52) U.S. Cl. .................. 600/361; 600/306; 600/300; 600/301; 324/438; 436/68; 204/433; 204/228.6

(58) Field of Classification Search ........... 600/300, 600/301, 302, 306, 307, 361, 345, 348; 73/29.01; 324/438
See application file for complete search history.

(56) References Cited

U.S. PATENT DOCUMENTS

| 6,372,951 B1 * | 4/2002 | Ter-Ovanesyan et al. ... 604/361 |
| 6,869,430 B2 * | 3/2005 | Balbierz et al. ............. 606/41 |
| 7,025,765 B2 * | 4/2006 | Balbierz et al. ............. 606/41 |
| 2004/0171962 A1 * | 9/2004 | Leveque et al. ............ 600/547 |

\* cited by examiner

*Primary Examiner*—Charles A. Marmor, II
*Assistant Examiner*—Navin Natnithithadha
(74) *Attorney, Agent, or Firm*—Michael Klicpera

(57) ABSTRACT

The present invention pertains to an apparatus for evaluating the signal strength from the pH sensor to determine whether the sensor is hydrated sufficiently to accurately measure pH. This is accomplished by utilizing circuitry that periodically sends a low voltage signal to a suitable pH sensor and then receiving the resulting waveforms which are analyzed by a processing receiver. The electrical connection between a suitable pH sensor and hydration monitoring circuitry is generally hard wired. In one embodiment, a processing receiver is coupled with the hydration monitoring circuitry as a single apparatus. In a second embodiment, the processing receiver can be independent and located remote from the hydration monitoring circuitry. In this embodiment, the hydration monitoring circuitry and the processing receiver are electrically connected using either hard wired techniques or wireless technology. In addition, the processing receiver can include data recording capability.

13 Claims, 3 Drawing Sheets

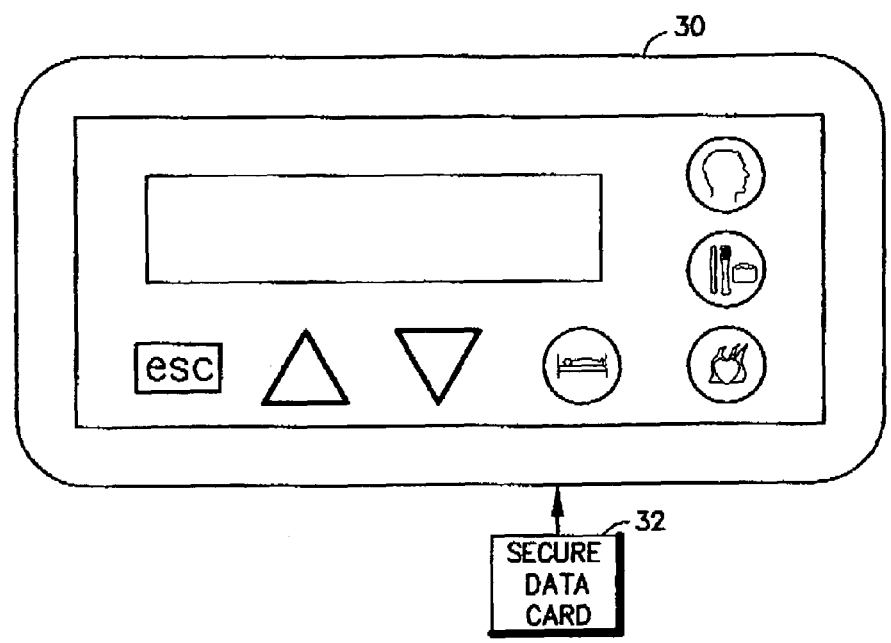
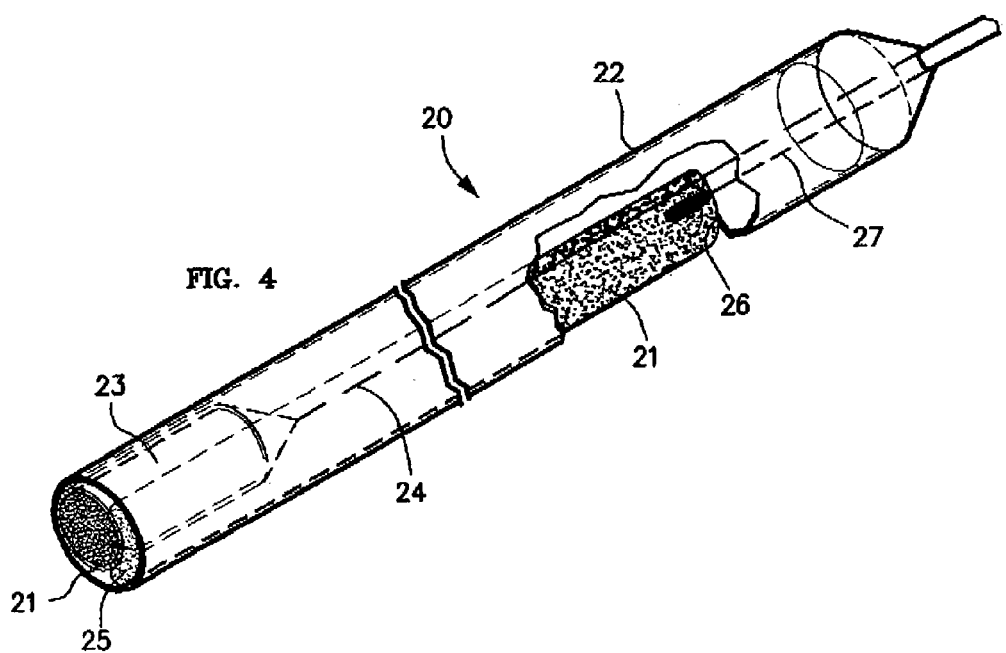

HYDRATION MONITORING CIRCUITRY FOR PH SENSORS

FIELD OF THE INVENTION

The field of art to which this invention relates is in the monitoring of pH using a sensor in corporeal and industrial applications. More specifically, the present invention monitors and detects the hydration level of pH sensors for determining the accuracy and strength of data generated from the sensor.

BACKGROUND OF THE INVENTION

Certain clinical methods and apparatus are known in the prior art for 24 hour monitoring of intra and supra esophageal pH in patients with suspected reflux disease or laryngopharyngeal disorders.

An example of a system for ambulatory 24 hour recording of gastroesophageal reflux is the Digitrapper™ System (manufactured by Synectics Medical AB, in Stockholm, Sweden) used with glass or Monocrystant™ pH catheters (as described in U.S. Pat. No. 4,119,498) and with the analysis software EsopHogram™ (by Gastrosoft, Inc. in Dallas, Tex.). These prior art systems typically measure pH in the esophageal tract with an intra-esophageal catheter and generate reports regarding esophageal exposure of gastric fluid. Systems such as these are primarily designed to measure reflux moving past the Lower Esophageal Spincter (LES) into the esophagus.

Sensors that measure and detect reflux above the Upper Esophagel Spincter (UES) have been less successful due to problems with traditional pH sensors malfunctioning when direct fluid contact is lost. Problems such as drift and artifacts (sometimes referred to as pseudoreflux events) are common complaints when attempting to measuring pH above the UES.

Currently there are no pH monitoring devices that teach how or have the capability to simultaneously measure pH data, monitor a pH sensors level of hydration and determine the reliability of the measurement Because all pH sensors require moisture to function, one way to determine if the sensor is functioning properly would be to detect the presence of a liquid through the use of electrical impedance. One such system as described by Anders Essen-Moller, (U.S. Pat. No. 5,479,935) detects the presence or absence of liquid reflux through the use of separate electrical electrodes incorporated into a catheter that is inserted into the esophagus. These catheters require dedicated electrodes and additional circuitry to function properly which increases cost and complexity. Additionally, because it is not directly connected to the pH sensor, it can only infer that the pH sensor is working reliably and the data is accurate if adequate levels of hydration are detected.

SUMMARY OF THE INVENTION

The present invention pertains to an apparatus for evaluating the signal strength from a suitable pH sensor to determine whether the sensor is hydrated sufficiently to accurately measure pH. This is accomplished by utilizing a novel circuitry that periodically sends a low voltage signal to a suitable pH sensor and then receiving the resulting waveforms which are analyzed by a processing receiver. The electrical connection between a suitable pH sensor and hydration monitoring circuitry is generally hard wired. In one embodiment, a processing receiver is coupled with the hydration monitoring circuitry as a single apparatus. In a second embodiment, the processing receiver can be independent and located remote from the hydration monitoring circuitry. In this embodiment, the hydration monitoring circuitry and the processing receiver are electrically connected using either hard wired techniques or wireless technology. In all embodiments of the present invention, the monitoring and monitoring of the hydration level is conducted in real-time. In addition, the processing receiver can include data recording capability.

It is the object with the present invention to provide a means of which a specialized circuitry, when used in combination with a suitable pH sensor, can be used to determine adequate signal strength for reliable pH measurement.

These and other features, aspects and advantages of the present invention will become better understood with reference to the following descriptions and claims.

BRIEF DESCRIPTION OF THE DRAWINGS

FIG. 2 is a perspective representation of a processing receiver with optional data recording capability.

FIG. 4 is one example of a pH sensor that is suitable for monitoring of hydration and signal strength using the hydration monitoring circuitry and the processing receiver.

DESCRIPTION OF THE PREFERRED EMBODIMENTS

Figure 1:
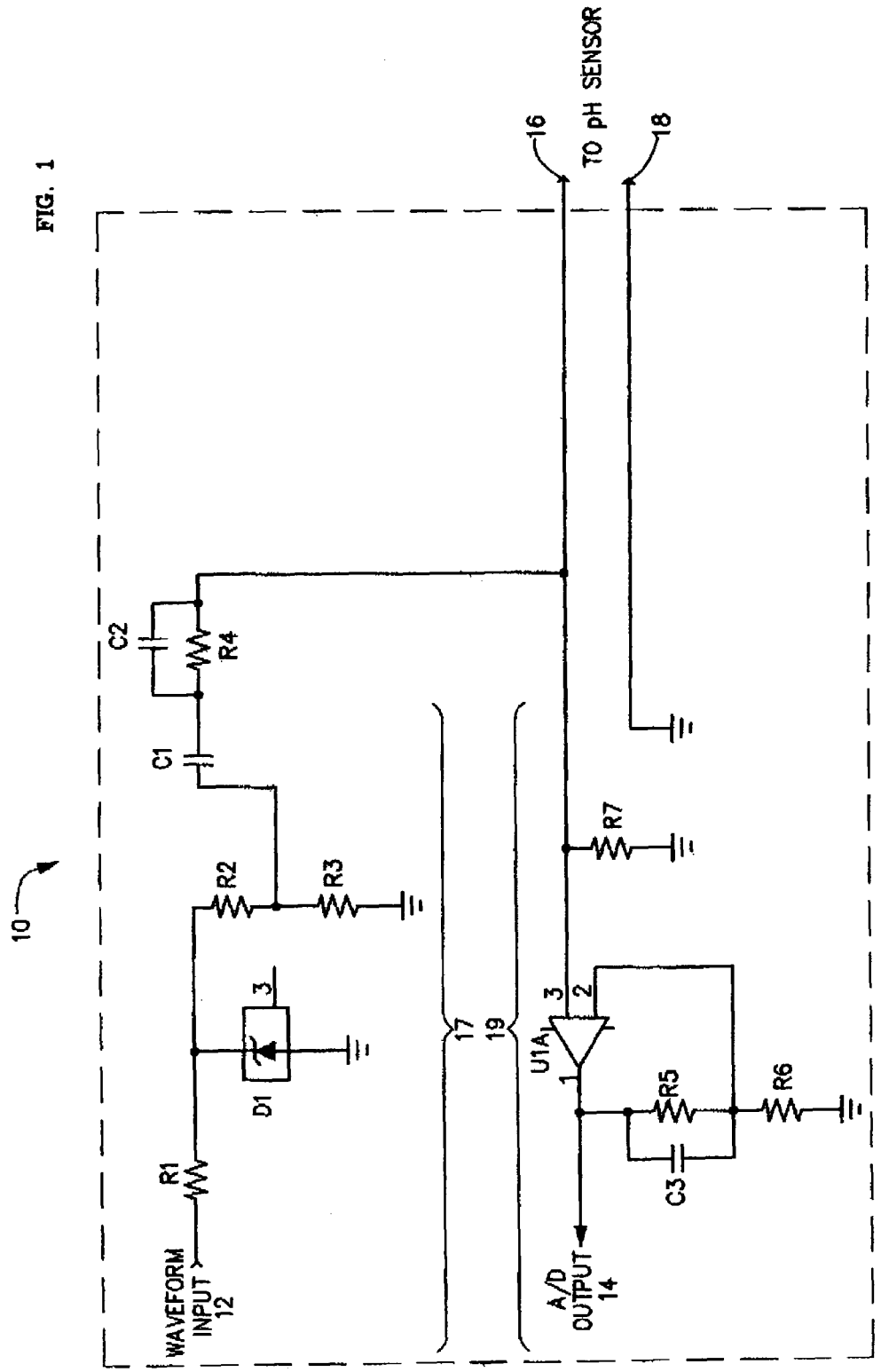
FIG. 1 is a schematic representation of the electrical circuit used in the transmitting device for monitoring the hydration level of a suitable pH sensor.

FIG. 1 demonstrates a schematic representation of a hydration monitoring circuit 10 used for monitoring and detecting the hydration level of a suitable pH sensor 20. The hydration monitoring circuit 10 periodically (or on a specified periodic frequency) sends a small electrical waveform (approximately 0.5V Peak to Peak waveform) through input circuitry 12 and electronic communication means 16, 18 to a suitable pH sensor 20. After the low voltage signal is sent to the suitable pH sensor 20, circuitry 14 outputs the resulting waveforms that can be used to detect fully hydrated, partially hydrated and non-hydrated conditions. If the analysis of the data shows a relatively stable reading from peak to peak (generally than 80 millivolts P—P) the pH data is accepted and can be recorded. If the data shows a relatively high peak to peak reading the recording of pH data can be terminated and the apparatus can signal visually or audibly that the data may be unreliable.

FIG. 2 is a perspective representation of a processing receiver 30 with optional data recording capability 32. The processing receiver 30 is typically designed as the operator interface between both the clinician and patient, and can include a means for recording pH data and user events during an ambulatory study. The processing receiver 30 is usually battery powered, and includes a clock to keep and display time, memory to store patient data, buttons for recording patient events, and an electronic connection to a hydration monitoring circuitry 10. This electronic connection can be wired or wireless. Additionally, the recorder typically provides a way to upload the data to a PC for storage and analysis.

The processing receiver 30 includes one or more microprocessors that are typically low power devices such as Microchip model 16F and 18F series controllers, and the ATMEL 8051 family of devices. Timekeeping can be accomplished by the microprocessor, or accomplished by a dedicated time chip such as the Dallas DS1338 real time clock. To keep power consumption to a minimum, LCD displays such as the Optrex DMC-16204 can be utilized. Wireless communication can be accomplished in a variety of means, from frequency shift keying techniques to advanced spread spectrum designs.

The processing receiver 30 includes software that is specifically designed to analize waveforms generated by the output 14 of the hydration monitor circuitry 10. The software is programmed to initiate a visual audible alarm and/or stop recording pH data upon the occurrence of unreliable waveforms. Furthermore, the processing receiver 30 can have the capability to monitor and record pH data, in real time, generated by the pH sensor. Both the hydration monitoring data and the pH data obtained from the sensor can be further downloaded onto the recording capability 32. Recording capability 32 can be one of the typical marketed non-volatile memory devices such as Secure Digital™ (SD), Multimedia Card™ (MMC), Compact Flash™, Smart Media™, or can be propietary developed data card. Other types or non-volatile media that can be used as recording capability 32 are CD-ROMs, DVDs, and hard disks.

Figure 3:
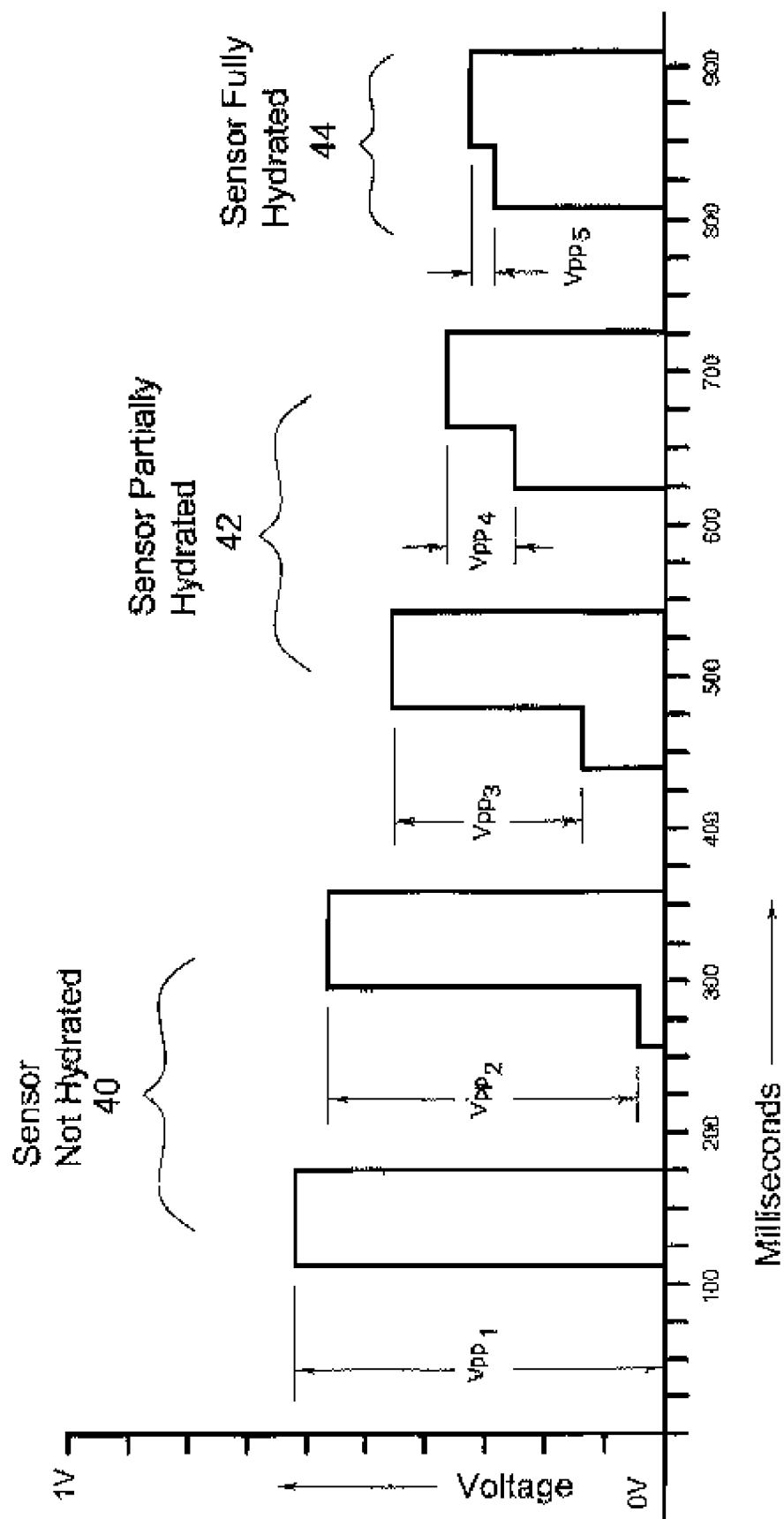
FIG. 3 is a graphic representation of the hydration monitoring waveform demonstrating the expected wave format for a non-hydrated, partially hydrated and fully hydrated suitable pH sensor.

FIG. 3 is a graphic representation of the hydration monitoring results demonstrating the expected wave format for non-hydrated 40 (see $Vpp_1$ and $Vpp_2$), partially hydrated 42 (see $Vpp_3$ and $Vpp_4$), and fully hydrated 46 (see $Vpp_5$) states of the pH sensor (where $Vpp_x$ represents the voltage ratio peak to peak). On the left side of the graph, the waveform 40 demonstrates that the suitable pH Sensor is not hydrated. In the middle of the graph, the waveform 42 demonstrates that the suitable pH Sensor is partially hydrated. On the right side, the waveform 46 demonstrates that the suitable pH Sensor is fully hydrated. If the suitable pH sensor loses hydration or malfunctions, data generated may be unreliable. The hydration monitor circuit 10 periodically sends a low voltage signal through input circuitry 17 and electronic communication means 16, 18 to the pH sensor 20. After the low voltage signal is sent to the pH sensor 20, output circuitry 19 sends the composite signal to the processing receiver 30 for analyzing the resulting waveforms.

FIG. 4 is just one example of a pH sensor that is suitable for hydration monitoring. This pH sensor is being provided only for the purpose of an example as the Applicants assert that other pH sensor designs can utilize and benefit from the present invention. For this purpose, the example pH sensor is a self-condensing design with an outer tubular member 21 and an inner tubular member 22. Both are usually fabricated by an extrusion or dip coating process using a variety of polymeric materials. Located within the inner tubular member 22 is an antimony element 23. The antimony element 23 is engaged at its proximal end to an electronic communication means 24. A reference wick 25 is located between the inside surface of the outer tubular member 21 of the example pH sensor 20 and the outer surface of the inner tubular member 22. The reference wick 28 is impregnated with an ion conduction fluid 28. Typical conduction fluids include those that contain sodium chloride or potassium chloride and water. Located proximally, from the proximal end of the antimony element 23 is a reference element 26. Said reference element 26 is primarily composed of a silver core surrounded with a coating of silver chloride. The reference element 26 is engaged to an electrical communication means 27, e.g. typical wire that extends to the proximal end of the outer tubular member and terminates in a typical electrical connector.

We claim:

1. An apparatus for monitoring the hydration level of a pH sensor, said apparatus comprising:
   a pH sensor;
   a hydration monitoring circuit for monitoring the hydration level of said pH sensor and for outputting a waveform indicative of the hydration level;
   an eletrically communication means between said hydration monitoring circuitry and said pH sensor; and
   a processing receiver, said processing receiver in communication with said hydration monitoring circuitry.

2. The apparatus for monitoring the hydration level as recited in claim 1, further comprising that said processing receiver includes a data recorder.

3. The apparatus for monitoring the hydration level as recited in claim 1, wherein said hydration monitoring circuitry and said processing receiver is incorporated in a single apparatus.

4. The apparatus for monitoring the hydration level as recited in claim 1, wherein said hydration monitoring circuitry monitors said hydration level on a specified periodic frequency.

5. The apparatus for monitoring the hydration level as recited in claim 1, wherein said processing receiver is in real time communication with said hydration monitoring circuitry.

6. The apparatus for monitoring the hydration level as recited in claim 1, wherein said processing receiver is in wireless communication with said hydration monitoring circuitry.

7. The apparatus for monitoring the hydration level as recited in claim 6, wherein said wireless communication is conducted in real-time.

8. the apparatus for monitoring the hydration level as recited in claim 1, wherein said processing receiver has the capability to analyze the hydration level of a self-condensing sensor.

9. The apparatus for monitoring the hydration level as recited in claim 2, further comprising a removable data storage medium, said removable data storage designed to communicate with said processing receiver with data recorder, said removable data storage medium further designed to store recorded pH measurements monitored by said self-condensing pH sensor over a period of time.

10. The apparatus for monitoring of pH as recited in claim 1, wherein said processing receiver includes a visual or audible alarming means that is generated if the sensor is not sufficiently hydrated to provide reliable pH measurements.

11. The apparatus for monitoring of pH as recited in claim 1, wherein said processing receiver includes a visual or audible alarming means that is generated upon the occurrence of a specific waveform.

12. The apparatus for monitoring of pH as recited in claim 1, wherein said processing receiver includes a means for terminating the recording of pH data if said data shows a relatively high peak to peak reading indicating that the pH sensor is not providing reliable pH measurements.

13. An apparatus for monitoring the hydration level of a pH sensor, said apparatus comprising:
   a hydration monitoring circuit;
   a pH sensor;
   an electrcally communication means between said hydration monitoring circuitry and said pH sensor; and
   a processing receiver, said processing receiver in communication with said hydration monitoring circuitry; and
   an algorithm to determine if said pH sensor is sufficiently hydrated to provide reliable pH measurements.

* * * * *